US009465983B2

United States Patent
Foertsch et al.

(10) Patent No.: US 9,465,983 B2
(45) Date of Patent: Oct. 11, 2016

(54) METHOD AND IMAGING APPARATUS TO AUTOMATICALLY DISPLAY AND/OR MEASURE BONE VARIATIONS IN MEDICAL IMAGE DATA

(71) Applicant: Siemens Aktiengesellschaft, Munich (DE)

(72) Inventors: Stefan Foertsch, Kunreuth (DE); Dominik Paul, Bubenreuth (DE); Susanne Schmolke, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/482,132

(22) Filed: Sep. 10, 2014

(65) Prior Publication Data

US 2015/0071519 A1    Mar. 12, 2015

(30) Foreign Application Priority Data

Sep. 10, 2013   (DE) ........................ 10 2013 218 047

(51) Int. Cl.
| | |
|---|---|
| *G06K 9/00* | (2006.01) |
| *A61B 5/055* | (2006.01) |
| *A61B 5/00* | (2006.01) |
| *G06T 7/00* | (2006.01) |
| *A61B 6/03* | (2006.01) |
| *A61B 6/00* | (2006.01) |
| *A61B 8/08* | (2006.01) |

(52) U.S. Cl.
CPC ........... *G06K 9/00362* (2013.01); *A61B 5/055* (2013.01); *A61B 5/4504* (2013.01); *A61B 6/032* (2013.01); *A61B 6/505* (2013.01); *A61B 6/5217* (2013.01); *A61B 8/0875* (2013.01); *A61B 8/5223* (2013.01); *G06T 7/0014* (2013.01); *G06T 7/0083* (2013.01); *G06T 2207/10088* (2013.01); *G06T 2207/30008* (2013.01)

(58) Field of Classification Search
None
See application file for complete search history.

(56) References Cited

U.S. PATENT DOCUMENTS

| | | | | |
|---|---|---|---|---|
| 7,876,938 | B2 * | 1/2011 | Huang | G06T 7/0028 382/128 |
| 2003/0215120 | A1 * | 11/2003 | Uppaluri | A61B 6/482 382/128 |
| 2005/0163358 | A1 * | 7/2005 | Moeller | G06K 9/342 382/128 |
| 2008/0019580 | A1 * | 1/2008 | Ohyu | G06K 9/3216 382/130 |
| 2010/0134517 | A1 * | 6/2010 | Saikaly | G06T 7/0012 345/619 |
| 2013/0060121 | A1 | 3/2013 | Patwardhan et al. | |

* cited by examiner

*Primary Examiner* — Siamak Harandi
*Assistant Examiner* — Amandeep Saini
(74) *Attorney, Agent, or Firm* — Schiff Hardin LLP

(57) ABSTRACT

In a method and apparatus to automatically display and/or measure bone variations in medical image data, an image data set of an examination region is acquired and the bone regions in the image data set are automatically segmented in a first segmentation followed by a second segmentation in which bone variation regions in the image data set are automatically segmented on the basis of the results of the first segmentation. The results of the first and/or second segmentations are stored and/or displayed.

19 Claims, 2 Drawing Sheets

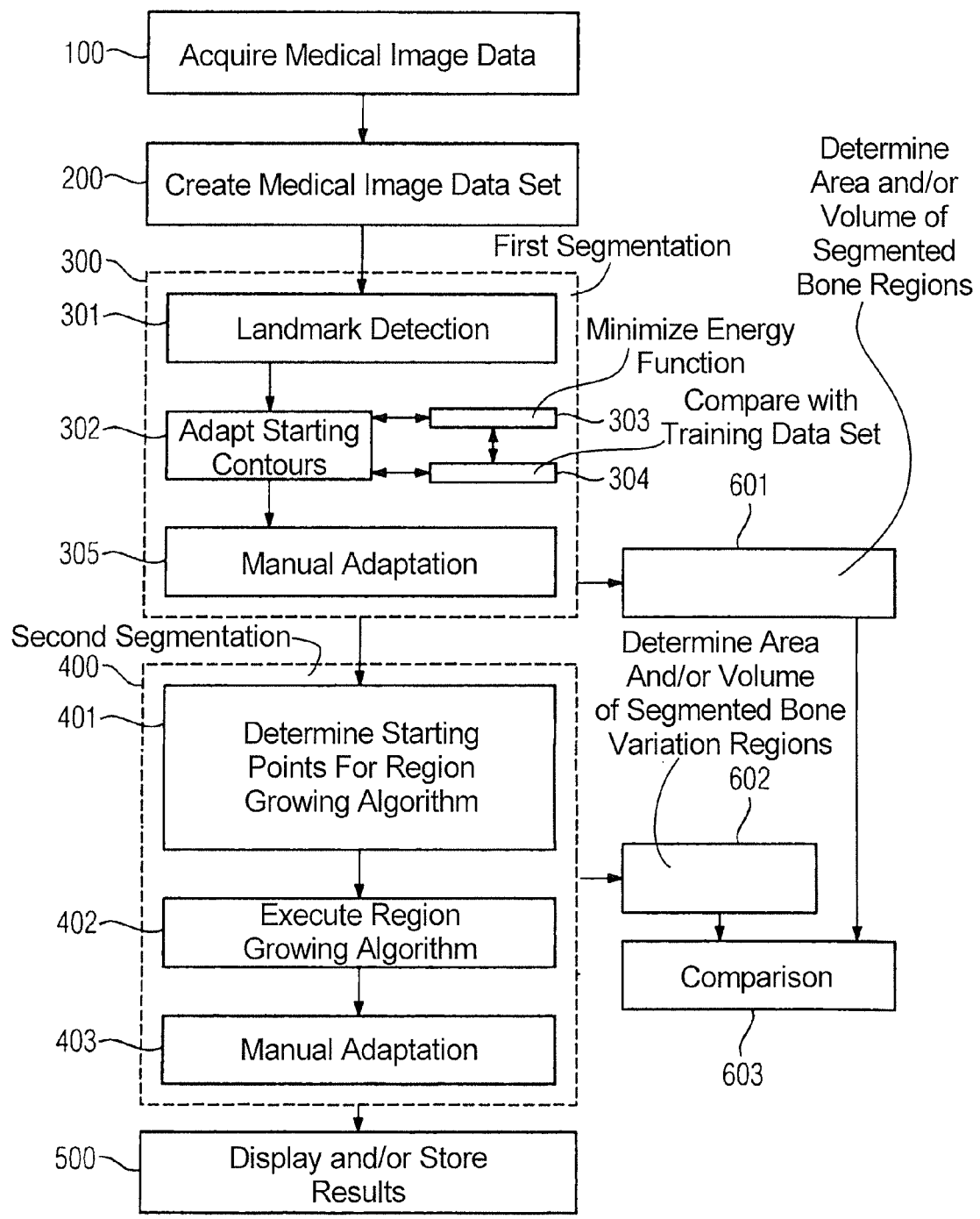

METHOD AND IMAGING APPARATUS TO AUTOMATICALLY DISPLAY AND/OR MEASURE BONE VARIATIONS IN MEDICAL IMAGE DATA

BACKGROUND OF THE INVENTION

1. Field of the Invention

The present invention concerns: a method to automatically display and/or measure bone variations in medical image data; as well as a medical imaging apparatus; a computer program product; and an electronically readable data storage medium to implement such a method.

2. Description of the Prior Art

Medical image data typically are acquired to assess the condition of bones in the human body and to display bone variations. For example, a joint examination (of the hand, for example) is typically implemented in the examination of inflammatory joint illnesses such as rheumatoid arthritis. One parameter in these examinations is the assessment of bone erosions. The assessment of the bone erosions currently takes place on a qualitative basis in which an observer grades the degree of the erosion using a scale. However, this method is affected by the experience and subjectivity of the observer, and thus hinders the comparability and the evaluation of changes in the course of the illness.

SUMMARY OF THE INVENTION

An object of the invention is to provide a method that enables display and/or measurement of bone variations in medical image data in order to facilitate an evaluation of the bone variations by a trained observer (by a physician, for example).

The method according to the invention to automatically display and/or measure bone variations in medical image data includes the following steps:

An image data set of an examination region is acquired and is provided to a computerized processor.

A first segmentation step is implemented in the processor that automatically segments the bone regions in the image data set.

A second segmentation step is implemented in the processor that automatically segments bone variation regions in the image data set on the basis of the results of the first segmentation step.

The results of the first and/or second segmentation step are displayed and/or stored.

The acquisition of the image data set can be implemented with the contemporaneous acquisition of the image data set by a medical imaging apparatus, but the acquisition of the image data set can also be the importation of preexisting exposures to the processor that have been acquired by a medical imaging apparatus. Such a medical imaging apparatus can be a magnetic resonance apparatus, a computed tomography apparatus, an x-ray apparatus, or an ultrasound apparatus. The medical imaging apparatus can also be a combination of different medical imaging apparatuses. The image data set can be three-dimensional, or one or more two-dimensional slice images. The examination region should include bones of a human or an animal.

The bone regions are typically those regions in the examination region that include bone structures. The bone regions include the variations of the bone structures. The bone variation regions are typically those regions in the examination region that include variations of the bone structures. The bone variation regions are typically a portion of the bone regions. Variations of the bone structures can be inflammatory bone variations that may have been caused by rheumatoid arthritis, in which case the variations of the bone structures are erosions of the bones. Such variations can also be edema from which erosions can arise in the course of the illness. The variations of the bone structures can differ by measurable parameters in the image data set of the bone structures. Such a measurable parameter is typically the intensity in the image data set.

The segmentation of the bone regions or bone variation regions can include the determination of a partial region of the examination region which includes said bone regions or bone variation regions. The segmentation of the bone variation regions thus builds on the preceding segmentation of the bone regions. The bone regions can thereby define the region in which the bone variation regions are located. In the examination region, multiple bone regions or bone variation regions that are demarcated from one another can occur.

The bone regions and bone variation regions can be detected in a standardized process. For a trained observer, a better comparability of the segmented regions between different patients, or between multiple exposures of a patient, is achieved than given a manual detection. Better monitoring of progression bone variations by a trained observer can be achieved with the method, even in long-term studies. The method can also be used to facilitate progression monitoring and for facilitated assessment and better control of a therapy. Smaller bone variations can be determined directly by an absolute quantitative measure.

If the method is used to facilitate a progression monitoring of bone variations, to facilitate an assessment and control of a therapy, or to facilitate a comparison of the bone variations of different patients, it is thus helpful to position the examination region for the acquisition of the image data sets at an established position in the medical imaging apparatus. The examination region can simultaneously be positioned for the acquisition of the image data sets at an established position in the medical imaging apparatus. The established position can be a standardized position and can be specified by means of coordinates in three spatial directions relative to a reference point of the medical imaging apparatus.

Measurable parameters of the bone variations in the image data sets can advantageously be compared automatically with the method. The method thus facilitates an automatic and normalized comparison of bone variations in large patient populations by trained specialists. An assessment of success of a particular therapy can also be facilitated with the method. The control of a therapy can be facilitated using the assessment and/or an acquisition of additional image data sets for an improved progression monitoring of a therapy can be initiated.

In an embodiment, the area and/or the volume of the bone regions is/are determined on the basis of the result of the first segmentation step. For this purpose, the bone regions (determined in the first segmentation step) in the image data set and the known resolution of the image data set can be used. In a two-dimensional image data set, the area of the bone regions can advantageously be determined. In a three-dimensional image data set, the volume of the bone regions can advantageously be determined. The area and/or the volume of the bone regions can be a measure relative to which the area and/or the volume of the bone variation regions can later be compared. If multiple bone regions demarcated from one another are present in the examination region, the area and/or the volume of the individual bone regions can be determined separately from one another, or the entire area and/or the entire volume of all bone regions can be determined.

In another embodiment, the area and/or the volume of the bone regions is/are determined on the basis of the result of the second segmentation step. For this purpose, the bone regions (determined in the first segmentation step) in the image data set and the known resolution of the image data set can be used. If multiple bone regions demarcated from one another are present in the examination region, the area and/or the volume of the individual bone variation regions can be determined separately from one another, or the entire area and/or the entire volume of all bone variation regions can be determined. Furthermore, among how many individual bone variation regions (demarcated from one another) the variations of the bone structures are distributed can be determined in this step.

In another embodiment, provides percentile proportion of at least one of the area, or of the volume of the bone variation regions in the area, or the volume of the bone regions, is calculated on the basis of the results of the first and second segmentation step. Here the percentile proportion of the entire area and/or of the entire volume of the bone variation regions in the entire area and/or the entire volume of the bone regions can also be determined again. However, it is also possible to determine that, for every bone region (which bone regions are demarcated from one another), the proportion of the area and/or of the volume of the bone variation regions (which lie in these bone regions) in the area and/or the volume of the bone.

In another embodiment, the bone regions and/or bone variation regions that is/are determined by the method are compared with bone regions and/or bone variation regions that is/are manually segmented by a user, and the results of the comparison are used in order to adapt defined parameters of the first and/or second segmentation step. The comparison of the regions determined by the method and the manually segmented regions can be executed automatically. The results of the comparison can be used in order to adapt defined parameters of the algorithms used by the method. The adaptation of the parameters can take place such that the regions determined by the method are adapted to the regions segmented by the user. The method can therefore be adaptive.

In another embodiment, the acquisition of the image data set is implemented by means of a magnetic resonance apparatus. Morphological magnetic resonance acquisitions offer the possibility of a high contrast between the bone structures and the variations of the bone structures. In the case of rheumatoid arthritis, magnetic resonance exposures are particularly advantageous since they can depict the morphology of the joint space. It is advantageous to use imaging parameters that produce a high contrast between bone regions and bone variation regions to acquire the medical image data. Therefore, it is easy for the method to demarcate the bone variation regions from the bone regions in a second segmentation step. In the case of magnetic resonance imaging, for example, an advantageous imaging sequence is a VIBE (volumetric interpolated breath-hold examination) sequence or SPACE (sampling perfection with application-optimized contrasts using different flip angle evolutions) sequence. Furthermore, in the case of magnetic resonance imaging the imaging sequences should include no fat saturation.

In another embodiment, the acquisition of the image data set is implemented with an isotropic resolution. The image data set can be acquired with an isotropic resolution. The image data set can also be reconstructed with an isotropic resolution. A greater reproducibility and precision are achieved by use of isotropic image data sets. Furthermore, partial volume effects can be reduced.

In another embodiment, the first segmentation step includes an automatic adaptation of starting contours to the contours of the bone regions. The starting contours can hereby be placed manually or automatically within the bone structures. A use of a respective starting contour per bone structure is reasonable if multiple bone structures demarcated from one another are present in the examination region. The starting contour can then be adapted by the algorithm until it corresponds to or strongly resembles the contour of the bone structure. The adaptation of the contour can take place in two dimensions or three dimensions. The adaptation of the contour can be implemented with suitable parameters so that the bone variation regions are segmented as part of the bone regions. It is advantageous for adaptation of the starting contour to take place using a snake algorithm, also known as an active contour algorithm. Furthermore, the user can be given the ability to retroactively modify and optimize the contour of the bone regions.

In another embodiment, the adaptation of the starting contours includes a minimization of an energy function. The minimum of the energy function can be achieved by the starting contour being optimally adapted to the contour of the bone regions. The energy function can include multiple different energies. The energy function can be a weighted sum of multiple energies. Possible energies are curvature energies (defined by the contour), or boundary energies (defined by the outer bone structure), or intensity energies. The energies can be weighted by means of suitable parameters such that the bone variation regions are segmented as part of the bone regions. For example, if the bone variation regions are erosions of the bone, the curvature energy can be weighted such that an indentation of the contour at the erosions increases the energy and thus is energetically disadvantageous. An indentation of the contour at the bone erosions can thus be avoided, and the bone erosions can be segmented as part of the bone.

In another embodiment, the adaptation of the starting contours includes a comparison of the contours of the bone regions with models of contours of bone regions of a training data set. The models of the contours of the bone structures can have been extracted from other medical image data. Models of bone structures which exhibit bone variations (and thus are universally valid) can be of primary interest.

In another embodiment, the starting contours are determined by landmark detection. The landmark detection can be based on a difference of the intensity of the bone structures and the surrounding structures in the medical image data set. The starting contour can be placed within the bone structures. The size of the starting contour is typically selected such that it does not exceed the size of the respective bone structure. The possibility can be provided to the user to modify, delete or place the starting contours manually.

In another embodiment, the second segmentation step includes a region growing algorithm. The region growing algorithm can hereby utilize the differences between the bone variation regions and the bone regions in the medical image data in order to demarcate the bone variation regions from the bone regions. For example, the intensity difference can be used for this. Instead of the region growing algorithm, a snake algorithm (as in the first segmentation step) or another segmentation algorithm can be used.

In another embodiment, the determination of starting points of the region growing algorithm includes a use of the results of the first segmentation step and a threshold analysis. The results of the first segmentation step can be used as long as the starting points of the region growing algorithm must lie within the bone structures that show a modified structure of the bone. The threshold analysis can then compare the present intensities in the bone regions, and thus determine a suitable starting point for the region growing algorithm within a bone variation region. A starting point is typically set for every contiguous bone variation region. The user can be given the ability to manually modify, delete or place the starting points.

In another embodiment, reference shapes of the bone regions are determined in the segmented bone regions and reference shapes of the bone variation regions are determined in the segmented bone variation regions, and the distances between the reference shapes of the bone variation regions and the reference shapes of the associated bone regions are determined for said bone variation regions. A reference shape can be a reference point, a reference area or a reference volume. A reference shape can be a prominent structure in the bone region or bone variation region. Particularly in the case of rheumatoid arthritis, the reference shape of the bone region can be the area of the bone region which adjoins the joint space. The reference shape of the bone variation region can be the middle point of the bone erosion. In this case, the distance is thus determined between the middle point of the bone erosion and the joint space.

A medical imaging apparatus according to the invention for automatic display and/or measurement of bone variations has the following components:

An image data acquisition unit acquires an image data set of an examination region.

A first segmentation unit automatically segments the bone regions in the image data set.

A second segmentation unit automatically segments the bone variation regions in the image data set on the basis of the results of the first segmentation unit.

An output unit displays and/or stores the results of the first and/or second segmentation unit. The medical imaging apparatus according to the invention automatically segments bone regions and bone variation regions in an image data set acquired by the medical imaging apparatus. By such automatic segmentation, a better comparability of the segmented regions between different patients or between multiple exposures of a patient than given a manual segmentation is made possible for a trained observer.

The medical imaging apparatus can have a computer that is designed to execute the method according to the invention. The computer can be integrated into the medical imaging apparatus, or can be installed separately from the medical imaging apparatus. The computer can be connected with the medical imaging apparatus. With the computer, the medical imaging apparatus can execute all of the embodiments of the method according to the invention as described above. The computer of the medical imaging apparatus can execute at least portions of a method according to the invention and/or send control information to the medical imaging and/or receive control signals from the medical imaging apparatus, which control signals execute at least portions of a method according to the invention. For this purpose, the computer can have control components that are necessary and/or advantageous for the execution of a method according to the invention. Embodiments of the medical imaging apparatus according to the invention are designed to the embodiments of the method according to the invention.

The present invention also encompasses a non-transitory, computer-readable data storage medium encoded with programming instructions that, when the storage medium is loaded into a computer, cause the computer to execute all of various embodiments described above of the method according to the invention. The method according to the invention can be executed quickly, robustly and so as to be identically repeatable. The programming instructions may require supporting items (for example libraries and auxiliary functions) in order to realize the corresponding embodiments of the method. The programming instructions can be in source code (in C++, for example) that must still be compiled and linked or that only needs to be interpreted, or can be in an executable software code that has only still to be loaded into the corresponding computer for execution. The computer needs to have the requirements (for example a working memory, a graphics card or a logic unit) so that the respective method steps can be executed efficiently. The computer into which the storage medium is loaded can be directly connected with the medical imaging apparatus, or can be designed as part of the medical imaging apparatus.

Examples of such an electronically readable data storage medium are a DVD, a magnetic tape, a hard disk or a USB stick on which are stored electronically readable control information.

BRIEF DESCRIPTION OF THE DRAWINGS

FIG. 3 is a flowchart of an embodiment of the method according to the invention.

DESCRIPTION OF THE PREFERRED EMBODIMENTS

Figure 1:
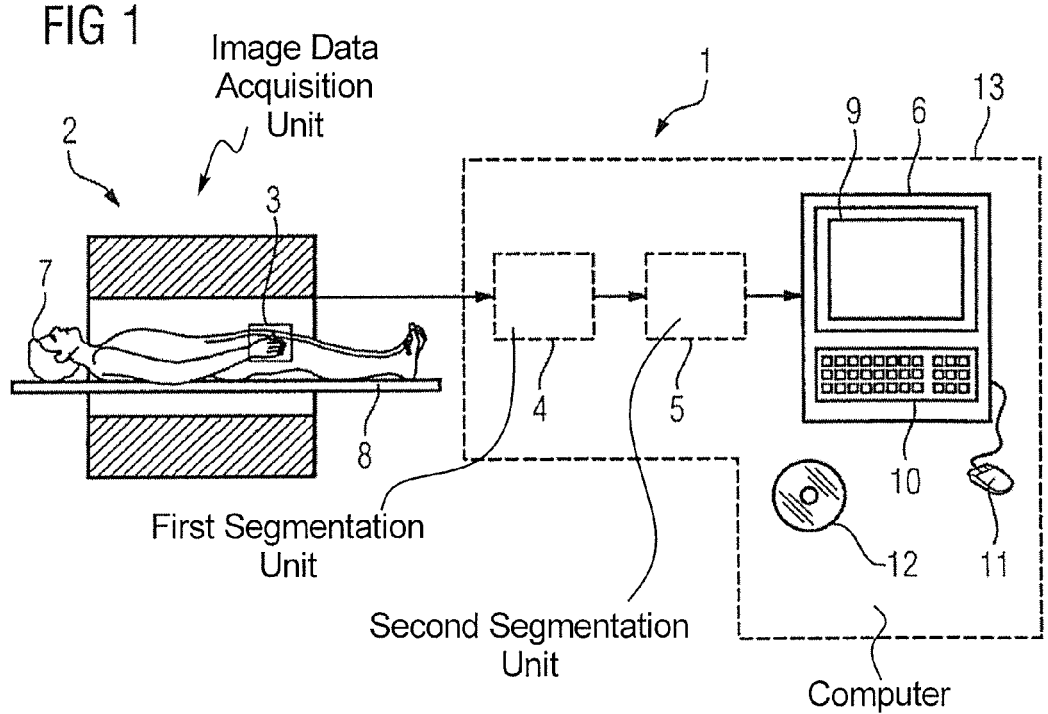
FIG. 1 schematically illustrates a medical imaging apparatus according to the invention that is designed to execute the method according to the invention.

FIG. 1 is a schematic presentation of a medical imaging apparatus 1 for execution of a method according to the invention. The medical imaging apparatus 1 includes an image data acquisition unit 2 to acquire an image data set of an examination region 3, a first segmentation unit 4 to automatically segment the bone regions in the image data set, a second segmentation unit 5 to automatically segment the bone variation regions in the image data set, and a terminal 6 to display, store and process the results of the first segmentation unit 4 and second segmentation unit 5. The terminal 6 has an output unit and an input unit. The terminal 6 in particular includes a monitor 9 and input devices, for example a keyboard 10 and a mouse 11. The medical imaging apparatus 1 furthermore has a computer 13 that includes the aforementioned first segmentation unit 4 and second segmentation unit 5, as well as the terminal 6.

The shown medical imaging apparatus 1 shown in FIG. 1 is a magnetic resonance apparatus. It has a tunnel-shaped opening in which a patient 7 is positioned on a patient support device 8. As noted above, the medical imaging apparatus 1 can also be a computed tomography apparatus, an x-ray apparatus or an ultrasound apparatus. Moreover, the medical imaging apparatus 1 does not necessarily need to have a patient support device 8 or a tunnel-shaped opening.

The shown examination region 3 is the hand of the patient. This is of particular interest if the method according to the invention should display bone variations due to rheumatoid arthritis. However, any other examination regions 3 of the patient 7 can also be examined by the medical imaging apparatus 1.

The medical imaging apparatus 1 (magnetic resonance apparatus) that is shown can naturally include additional components that medical imaging apparatuses 1 (magnetic resonance apparatuses) conventionally have. The general functioning of a medical imaging apparatus 1 (magnetic resonance apparatus) is known to those skilled in the art, so that a more detailed description is not necessary herein.

The medical imaging apparatus 1 is designed together with the computer 13 to execute embodiments of the method according to the invention including the embodiment shown in FIG. 3, wherein an automatic display and/or measurement of bone variations takes place in medical image data acquired by means of the medical imaging apparatus 1.

In a first method step 100, medical image data of an examination region 3 of the patient 7 are acquired by means of the image data acquisition unit 2 of the medical imaging apparatus 1, from which medical image data an image data set is created (advantageously with an isotropic resolution) in an additional method step 200. The image data acquisition unit 2 includes both the necessary hardware and the necessary software to acquire and create the image data set.

The image data set is then forwarded to the first segmentation unit 4, which automatically segments the bone regions in the image data set in a first segmentation step 300. The result of the first segmentation unit 4 is forwarded, together with the image data set, to the second segmentation unit 5. This segments the bone variation regions in the image data set which are part of the bone regions in a second segmentation step 400. Finally, the results of the first segmentation unit 4 and the second segmentation unit 5 are displayed at the terminal 6 and/or are stored by the computer 13 in an additional method step 500. The terminal 6 prepares the image data and the segmentation results such that they can be displayed at the monitor 9. A user can then navigate through the image data set and the result of the first segmentation unit 4 and the second segmentation unit 5 by means of the input devices 10, 11. A user can also participate in the method according to the invention via the input devices 10, 11, for example in that he retroactively modifies segmented regions or manually adapts the start contours and/or start points for the first segmentation step 300 or second segmentation step 400.

In a further method step 601, the area and/or the volume of the bone regions can be determined from the results of the first segmentation unit 4 by means of the computer 13. In a further method step 602, the area and/or the volume of the bone variation regions can be determined from the results of the second segmentation unit 5 by the computer 13. In a further method step 603, the proportion of the area and/or of the volume of the bone variation regions in the area and/or the volume of the bone regions can be determined by means of the computer 13 from the results of the first segmentation unit 4 and the second segmentation unit 5. The bone regions and bone variation regions that are determined by the method can be compared by means of the computer 13 with bone regions and bone variation regions that are manually segmented by a user by means of the input devices 10, 11, wherein the results of the comparison are used in order to adapt defined parameters of the first segmentation step 300 and second segmentation step 400.

The first segmentation step 300 begins with an additional method step 301 in which a landmark detection to determine the starting contours takes place by means of the first segmentation unit 4. A starting contour is individually established for each bone structure in the examination region. The starting contours are then adapted to the contours of the bone structures in an additional method step 302. An energy function is minimized in an additional method step 303 by the first segmentation unit 4, and a comparison of the starting contour with contours of bone structures of a training data set is implemented in an additional method step 304. The additional method steps 302, 303, 304 are repeated until the starting contour is optimally adapted to the contour of the bone structure. The adapted starting contour then represents a segmented bone region. A user is ultimately still provided with the possibility of adapting the segmented bone regions manually in an additional method step 305 by the input devices 10, 11.

The second segmentation step 400 starts with an additional method step 401 in which the automatic determination takes place within the bone variation regions. This takes place in the second segmentation unit 5 using a threshold analysis with the use of the result of the first segmentation step 300. Starting from the start points determined in method step 401, in an additional method step 402 executed by the second segmentation unit 5 a region growing algorithm detects the structures of bone variations in the image data set. A user is ultimately provided with the possibility to manually adapt the segmented bone variation regions in an additional method step 403 by the input devices 10, 11.

The method steps of the method according to the invention that are shown in FIG. 3 are executed by the computer 13 together with the medical imaging apparatus 1. For this, the computer 13 includes necessary software and/or computer programs that are stored in a memory unit of the computer 13. The software and/or computer programs include program items that are designed to execute methods according to the computer program and/or software is executed in the computer 13 by a processor unit of the medical imaging apparatus 1. Electronically readable control information can be stored on an electronically readable data medium 12 (a DVD, for example). The control information is designed such that it implements a method according to the invention given use of the electronically readable data medium 12 in a computer system.

Figure 2:
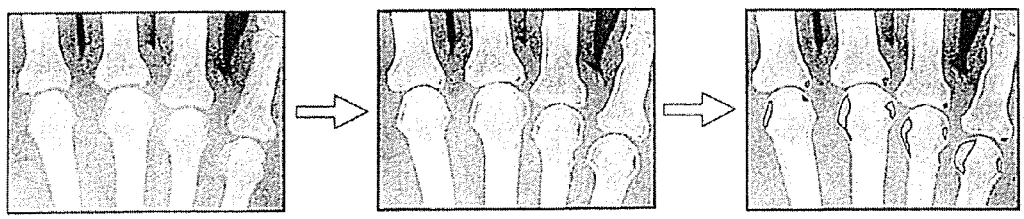
FIG. 2 shows slice images of an example of a magnetic resonance exposure of the hand without segmentation by means of the method, with segmentation of the bone regions, and with segmentation of the bone variation regions.

FIG. 2 shows a slice image of an example of a magnetic resonance exposure of the hand in three-fold execution: without segmentation by means of the method according to the invention (left), with segmentation of the bone regions with a white contour (middle), and with segmentation of the bone variation regions with a black contour (right). The left arrow hereby stands for the first segmentation step of the method which automatically segments the bone regions in the image data set. The right arrow stands for the second segmentation step of the method which automatically segments the bone variation regions on the basis of the results of the first segmentation step.

The advantageous use of the method with regard to medical image data of a patient with rheumatoid arthritis is shown in FIG. 2. A hand having bone structures that appear to be modified by rheumatoid arthritis has been selected as an examination region. An examination of the ankles or knee joints is also reasonable in the further course of rheumatoid arthritis. In the shown example, the metacarpophalangeal joints which connect the metacarpals with the proximal phalanges of the fingers have been examined. The proximal phalanges are also the typical examination region given clinical questions with regard to rheumatoid arthritis.

In the shown example, the variations of the bone structures are erosions of the bone near the joints. After the first segmentation step, they are segmented as shown, still as part of the bone regions. In the second segmentation step, for example, they are segmented as bone variation regions due to their different intensity in the image data. The segmentation of the bones and erosions therefore allows the quantitative proportion of the erosions at the bones to be determined automatically. Reference points of the bones can also be determined in the segmented bone regions, and the distances between the reference points of the bone variation regions and the reference points of the associated bone regions can be determined for the bone variation regions. This procedure can provide additional information about the bone variations with regard to the bone regions.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to automatically display bone variations in medical image data, comprising:
   providing a medical image data set to a computerized processor, said medical image data set representing an examination region of a subject that comprises bone regions and bone variation regions within said bone regions;
   in said processor, implementing a first segmentation of said image data set in which said bone regions in said image data set are automatically segmented and preserved;
   in said processor, implementing a second segmentation in which said bone variation regions in said segmented and preserved bone regions in said image data set are automatically segmented from the bone regions segmented in said first segmentation and are preserved individually so as to be separable from the preserved segmented bone regions; and
   displaying said segmented and preserved bone variation regions from said second segmentation at a monitor in communication with said processor.

2. A method as claimed in claim 1 comprising, in said processor, determining at least multi-dimensional size, selected from the group consisting of area and volume, of said bone regions from the segmentation thereof in said first segmentation.

3. A method as claimed in claim 1 comprising, in said processor, determining at least one multi-dimensional size, selected from the group consisting of area and volume, of the segmented bone variation regions from said second segmentation.

4. A method as claimed in claim 1 comprising, in said processor, determining a multi-dimensional size, selected from the group consisting of area and volume, of each of the segmented bone regions from said first segmentation and of each of the segmented bone variation regions from said second segmentation, and determining a percentile proportion of said multi-dimensional size of said bone variation regions to said multi-dimensional size of said bone regions.

5. A method as claimed in claim 1 comprising manually segmenting at least one of said bone regions and said bone variation regions in said data set and comparing said at least one manually segmented bone region or bone variation region to a corresponding at least one of the automatically segmented bone region or bone variation region, to obtain a comparison result, and using said comparison result to adapt segmentation parameters in at least one of said first segmentation or said second segmentation.

6. A method as claimed in claim 1 comprising providing a magnetic resonance image data set to said processor, as said image data set of said examination region.

7. A method as claimed in claim 1 comprising providing an image data set with isotropic resolution to said processor, as said image data set of said examination region.

8. A method as claimed in claim 1 comprising, in said first segmentation, automatically adapting starting contours of contours of said bone regions.

9. A method as claimed in claim 8 comprising adapting said starting contours by minimization of an energy function.

10. A method as claimed in claim 8 comprising adapting the starting contours by comparing the contours of the bone regions with models of contours of corresponding bone regions of a training data set.

11. A method as claimed in claim 8 comprising determining said starting contours of said bone regions by landmark detection in said image data set.

12. A method as claimed in claim 1 comprising executing said second segmentation by implementing a region growing algorithm.

13. A method as claimed in claim 12 comprising determining starting points of said region growing algorithm by applying a threshold analysis to said bone regions from said first segmentation.

14. A method as claimed in claim 1 comprising, in said processor, determining reference points of the bone regions from the segmented bone regions from said first segmentation, and determining reference points of said bone variation regions from the segmented bone variation regions from said second segmentation, and, for at least some of said bone variation regions, determining a distance between the reference points of the bone variation region and the reference points of the associated bone region.

15. A method as claimed in claim 1 comprising also displaying said segmented and preserved bone regions at said display, and displaying said segmented and preserved bone variation regions as designated regions within the displayed bone regions.

16. An apparatus to automatically display bone variations in medical image data, comprising:
   a computerized processor provided with a medical image data set, said medical image data set representing an examination region of a subject that comprises bone regions and bone variation regions within said bone regions;
   said processor comprising a first segmentation unit configured to implement a first segmentation of said image data set in which said bone regions in said image data set are automatically segmented and preserved;
   said processor comprising a second segmentation unit configured to implement a second segmentation in which said bone variation regions in said segmented and preserved bone regions in said image data set are automatically segmented from the bone regions segmented in said first segmentation and are preserved individually so as to be separable from the preserved segmented bone regions;
   a display monitor in communication with said processor; and said processor being configured to display said segmented and preserved bone variation regions from said second segmentation at said display monitor.

17. An apparatus as claimed in claim 16 wherein said processor is configured to also display the segmented and preserved bone regions at said display monitor, and to display said segmented and preserved bone variation regions as designated regions within the displayed bone regions.

18. A non-transitory, computer-readable data storage medium encoded with programming instructions, said storage medium being loaded into a computerized processor and said programming instructions causing said computerized processor to:

receive a medical image data set representing an examination region of a subject that comprises bone regions and bone variation regions within said bone regions;

implement a first segmentation of said image data set in which said bone regions in said image data set are automatically segmented and preserved;

implement a second segmentation in which said bone variation regions in said segmented and preserved bone regions in said image data set are automatically segmented from the bone regions segmented in said first segmentation and are preserved individually so as to be separable from the preserved segmented bone regions; and display said segmented and preserved bone variation regions from said second segmentation a monitor in communication with said computerized processor.

19. A data storage medium as claimed in claim 18 wherein said programming instructions cause said computerized processor to also display the segmented and preserved bone regions at said monitor, and to display the segmented and preserved bone variation regions as designated regions within the displayed bone regions.

\* \* \* \* \*